United States Patent
Sakamoto et al.

(10) Patent No.: US 7,981,284 B2
(45) Date of Patent: Jul. 19, 2011

(54) SUPPRESSOR UTILIZING MICRO ION EXCHANGE TUBE AND ION CHROMATOGRAPH UTILIZING THE SAME

(75) Inventors: Katsumasa Sakamoto, Kyoto (JP); Yukio Oikawa, Kyoto (JP); Shigeyoshi Horiike, Kyoto (JP); Hiroaki Nakanishi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 12/867,714

(22) PCT Filed: Feb. 21, 2008

(86) PCT No.: PCT/JP2008/052951
§ 371 (c)(1),
(2), (4) Date: Aug. 13, 2010

(87) PCT Pub. No.: WO2009/104262
PCT Pub. Date: Aug. 27, 2009

(65) Prior Publication Data
US 2010/0320132 A1    Dec. 23, 2010

(51) Int. Cl.
*B01D 15/08* (2006.01)
(52) U.S. Cl. ...... 210/198.2; 210/243; 210/635; 210/638; 210/656; 210/659; 204/632; 422/70; 436/161
(58) Field of Classification Search ......... 210/635, 210/638, 656, 659, 198.2, 243; 204/632, 204/638, 639; 422/70; 436/161
See application file for complete search history.

(56) References Cited

U.S. PATENT DOCUMENTS

| | | | |
|---|---|---|---|
| 4,403,039 A | 9/1983 | Ban et al. | |
| 4,486,312 A | 12/1984 | Slingsby et al. | |
| 4,751,004 A * | 6/1988 | Stevens et al. | 210/659 |
| 4,999,098 A | 3/1991 | Pohl et al. | |
| 5,352,360 A * | 10/1994 | Stillian et al. | 210/198.2 |
| 5,773,615 A * | 6/1998 | Small et al. | 436/161 |
| 6,328,885 B1 * | 12/2001 | Srinivasan et al. | 210/198.2 |
| 2002/0014446 A1 * | 2/2002 | Sugimoto et al. | 210/198.2 |
| 2008/0223787 A1 * | 9/2008 | Dasgupta et al. | 210/658 |

FOREIGN PATENT DOCUMENTS

| | | |
|---|---|---|
| JP | 57-74661 A | 5/1982 |
| JP | 60-100048 A | 6/1985 |
| JP | 61-172057 A | 8/1986 |
| JP | 5-52826 A | 3/1993 |

(Continued)

OTHER PUBLICATIONS

English language translation PTO 11-1834 of Japan Patent No. 07-012796.*

(Continued)

*Primary Examiner* — Ernest G Therkorn
(74) *Attorney, Agent, or Firm* — Cheng Law Group, PLLC

(57) ABSTRACT

Disclosed herein is a suppressor using one ion-exchange tube which has an inner diameter close to that of a tube connected to a separation column and which is constituted by an ion-exchange membrane. The ion-exchange tube is folded or wound more than once in a plane into a sheet form to provide an ion-exchange tube sheet through which an eluate from a separation column flows. The ion-exchange tube sheet is accommodated in a container. The container provides a regenerant flow channel so that a regenerant is allowed to flow on both sides of the ion-exchange tube sheet.

7 Claims, 3 Drawing Sheets

FOREIGN PATENT DOCUMENTS

| | | | |
|---|---|---|---|
| JP | 7-12796 A | | 1/1995 |
| JP | 7-012796 A | * | 1/1995 |
| JP | 8-29408 A | | 2/1996 |
| JP | 2002-513912 A | | 5/2002 |
| JP | 2002-214212 A | | 7/2002 |
| JP | 2002-228645 A | | 8/2002 |
| WO | WO-99/56849 A1 | | 11/1999 |

OTHER PUBLICATIONS

International Search Report for the Application No. PCT/JP2008/052951 mailed Mar. 18, 2008.

* cited by examiner

SUPPRESSOR UTILIZING MICRO ION EXCHANGE TUBE AND ION CHROMATOGRAPH UTILIZING THE SAME

REFERENCE TO RELATED APPLICATIONS

This application is a 371 of PCT/JP2008/052951 filed Feb. 21, 2008.

BACKGROUND OF THE INVENTION

1. Field of the Invention

The present invention relates to a suppressor for suppressing the background electrical conductivity of an eluate from a separation column of an ion chromatograph or for removing nontarget ions from a sample and an ion chromatograph for separation and analysis of inorganic ions or organic ions contained in a sample solution as one example of an analyzer utilizing such a suppressor.

2. Description of the Related Art

In an ion chromatograph, a sample is introduced into a separation column to separate it into component ions, and then the component ions are detected by measuring the electrical conductivity of an eluate from the separation column in an electrical conductivity measurement cell. In order to achieve high-sensitive measurement, a suppressor is provided between the separation column and the detector. The suppressor removes nontarget ions contained in an eluate from the separation column to reduce the electrical conductivity of the eluate.

A suppressor is used also in a sample pretreatment process to remove nontarget ions from a sample solution.

In a suppressor, ion exchange is performed to remove nontarget ions. Therefore, as a suppressor, one utilizing an ion-exchange column filled with an ion-exchange resin or one utilizing a planar ion-exchange membrane is used. In the case of an ion-exchange column-type suppressor, nontarget ions are removed through ion exchange by allowing a sample solution to pass through a column filled with an ion-exchange resin.

The ion-exchange column needs to be filled with a large amount of ion-exchange resin not only to increase its ion-exchange capacity but also to maintain its ion-exchange ability for a long period of time. However, filling the ion-exchange column with a large amount of ion-exchange resin leads to a larger inner diameter of the ion-exchange column than that of a tube connected to a separation column. This causes broadening of peak segments (bands), separated by the separation column, in the suppressor.

On the other hand, an ion-exchange membrane-type suppressor has two flow channels opposed to each other with an ion-exchange membrane being interposed between them. In the ion-exchange membrane-type suppressor, a sample solution is allowed to flow through one of the flow channels to remove nontarget ions through ion exchange using the ion-exchange membrane, and a regenerant is allowed to flow through the other flow channel to regenerate the ion-exchange membrane.

In the case of the ion-exchange membrane-type suppressor, its flow channel size can be made smaller as compared to the ion-exchange column-type suppressor. However, the flow channel of the ion-exchange membrane-type suppressor is rectangular in cross section, which changes flow conditions. Also in this case, broadening of peak segments occurs in the suppressor.

As a method for suppressing broadening of peak segments in a suppressor, one using an ion-exchange tube constituted by an ion-exchange membrane has been proposed (see U.S. Pat. No. 4,486,312). According to this method, an eluate from a separation column is allowed to flow inside the ion-exchange tube to perform ion exchange inside the tube to remove nontarget ions, and a regenerant is allowed to flow outside the ion-exchange tube to regenerate the ion-exchange membrane outside the tube. In this case, the inner diameter of the ion-exchange tube is made close to that of a tube connected to a separation column. This makes it possible to suppress broadening of peak segments in a suppressor.

The ion-exchange tube needs to be fixed in some way. For example, in the case of the method proposed in Patent Document 1, the tube is wound around a cylindrical core in the form of a coil, and a regenerant is allowed to flow along the wall of the coil. However, the winding of the tube around a core inevitably leads to an increase in the size of a suppressor. Further, the winding of the tube around a support such as a core makes it impossible to bring a regenerant into contact with the surface of the tube located on the support side. This reduces the regeneration efficiency of the ion-exchange membrane by a regenerant, and thus, ion-exchange performance is reduced.

SUMMARY OF THE INVENTION

It is therefore an object of the present invention to provide a suppressor capable of suppressing broadening of peak segments therein, easily reducing its size, and achieving high regeneration efficiency of an ion-exchange membrane, and an ion chromatograph utilizing such a suppressor.

The suppressor according to the present invention uses one ion-exchange tube which has an inner diameter close to that of a tube connected to a separation column and which is constituted by an ion-exchange membrane. The ion-exchange tube is folded or wound more than once in a plane into a sheet form to form an ion-exchange tube sheet through which an eluate from a separation column flows. The ion-exchange tube sheet is accommodated in a container. The container provides a regenerant flow channel so that a regenerant for regenerating ionic functional groups of the ion-exchange membrane flows on both sides of the plane of the ion-exchange tube sheet.

The ion-exchange tube sheet can be formed by, for example, folding the ion-exchange tube in a zigzag manner in a plane or winding the ion-exchange tube into a spiral or coil in a plane.

In a case where the suppressor is used for anion analysis, a cation exchange tube is used. The cation exchange tube is made of, for example, a perfluorocarbon polymer having an acidic functional group, such as a sulfonyl group or a carbonyl group, as an ionic functional group to exchange target cations for hydrogen ions ($H^+$). In a case where the suppressor is used for cation analysis, an anion exchange tube is used. The anion exchange tube is made of, for example, a perfluorocarbon polymer having a basic functional group, such as an ammonium group, as a functional group to exchange target anions for hydroxide ions ($OH^-$).

A regenerant supplies the ion-exchange membrane constituting the ion-exchange tube with hydrogen ions or hydroxide ions consumed by ion exchange.

In order to reduce the size of the suppressor, the container may be constituted by two substrates between which the ion-exchange tube sheet is to be interposed. In this case, both substrates each have a groove provided in each surface, and these two grooves are opposed to each other to form together the regenerant flow channel with the ion-exchange tube sheet being interposed between the grooves.

The concentration of hydrogen ions or hydroxide ions in a regenerant is reduced due to regeneration of the ion-exchange membrane. Therefore, it is preferred that the suppressor further includes a pair of electrodes for electrolyzing a regenerant, which are provided in the regenerant flow channel so as to be located on opposite sides of the plane of the ion-exchange tube sheet. The concentrations of hydrogen ions and hydroxide ions in a regenerant are increased by electrolyzing the regenerant by the passage of electric current through the electrodes.

In order to further reduce the size of the suppressor, the ion-exchange tube sheet is preferably formed by densely arranging the ion-exchange tube in a plane so that adjacent tube surfaces are in contact with each other.

The ion-exchange tube preferably has an inner diameter of 500 μm or less, more preferably 300 μm or less. The use of such an ion-exchange tube having a small inner diameter makes it possible to suppress the diffusion of a column eluate containing sample components in a flow channel. The flow rate of an eluent generally used in a high-pressure liquid chromatograph is in the range of 0.1 to 3 mL/min. In general, an ion-exchange membrane itself has an exchange capacity of about 95%. Therefore, in the case of a high-pressure liquid chromatograph, 90% or higher of cations or anions can be exchanged by increasing the retention time of an eluate in the ion-exchange tube by increasing the length of the ion-exchange tube according to the flow rate of an eluent.

The ion-exchange tube preferably has a wall thickness of 100 to 300 μM. The ion-exchange tube having a wall thickness within the above range can withstand a pressure of 1 to 3 MPa.

The ion-exchange tube may be made of a perfluorocarbon polymer having a functional group for ion exchange bonded thereto. This is because a perfluorocarbon polymer has high chemical resistance.

An ion chromatograph includes: a separation column; an eluent supply channel for supplying an eluent to the separation column; an injector provided in the eluent supply channel to inject a sample into the eluent supply channel; an electrical conductivity detector provided in an eluate flow channel through which an eluate from the separation column flows; and a suppressor provided in the eluate flow channel from the separation column between the separation column and the electrical conductivity detector. In the ion chromatograph according to the present invention, the suppressor of the present invention is used as the suppressor.

Since the ion-exchange tube has an inner diameter close to that of a tube connected to a separation column, broadening of peak segments in the ion-exchange tube can be suppressed.

Since the ion-exchange tube sheet is formed by folding or winding one ion-exchange tube more than once in a plane into a sheet form, the suppressor can be reduced in size.

In microanalysis, increased exchange capacity can be achieved due to an increased area of the wall surface of a flow channel. Further, since the ion-exchange tube sheet is not wound around a support, a regenerant is allowed to flow on both sides of the plane of the ion-exchange tube sheet. This makes it possible to bring a regenerant into contact with the ion-exchange membrane constituting the ion-exchange tube on both sides of the ion-exchange tube sheet to increase the area of contact between the regenerant and the ion-exchange membrane, thereby efficiently regenerating the ion-exchange membrane.

The suppressor according to the present invention has the function of desalination, and is therefore useful for pretreatment for mass analysis. Particularly, the ion-exchange tube having a very small inner diameter is very useful because a microscale sample is used in mass analysis.

The ion chromatograph according to the present invention equipped with such a suppressor can more effectively remove nontarget ions, which makes it possible to achieve high-sensitive ion chromatography.

Figure 1:
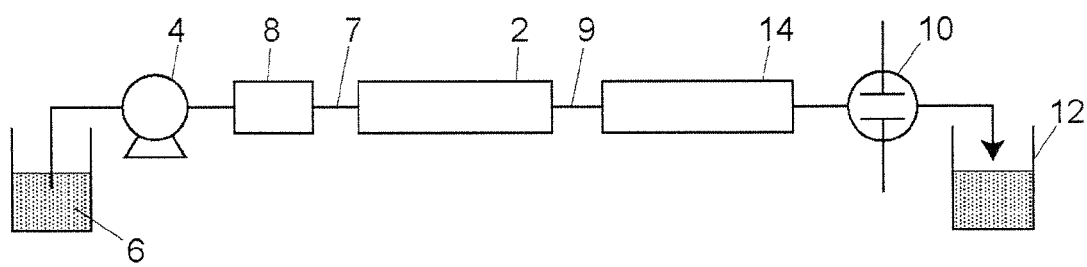
FIG. 1 is a schematic view showing the structure of one embodiment of an ion chromatograph according to the present invention.

DESCRIPTION OF THE REFERENCE NUMERALS 2 separation column
7 eluent supply channel
8 injector
9 tube connected to separation column
10 electrical conductivity measurement cell
14 suppressor
20 container
20a, 20b substrate
22 ion-exchange tube sheet
24 ion-exchange tube
36 regenerant flow channel
42 electrode

DETAILED DESCRIPTION OF THE INVENTION

FIG. 1 is a schematic view of one embodiment of an ion chromatograph according to the present invention. An eluent supply channel 7 equipped with a liquid pump 4 for supplying an eluent 6 is connected to a separation column 2. The eluent supply channel 7 is equipped also with an injector 8 for injecting a sample. A sample is introduced into the separation column 2 and separated into individual ions. The separation column 2 is connected to an eluate flow channel 9, and the eluate flow channel 9 is connected to an electrical conductivity measurement cell 10 of an electrical conductivity detector. An eluate from the separation column 2 is introduced into the cell 10 through the eluate flow channel 9. The electrical conductivity of the eluate is detected when the eluate passes through the cell 10. Effluent from the cell 10 is discharged into a drain 12.

In order to achieve high-sensitive measurement, a suppressor 14 is provided in the eluate flow channel 9 between the separation column 2 and the cell 10. The suppressor 14 can remove nontarget ions causing an increase in the electrical conductivity of a column eluate.

Figure 2:
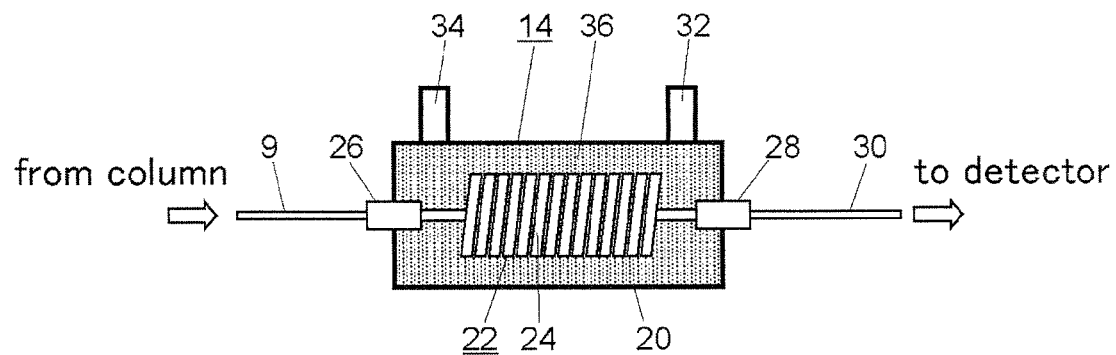
FIG. 2 is a schematic view of a suppressor used in the ion chromatograph shown in FIG. 1.

FIG. 2 is a schematic view of the suppressor 14. The suppressor 14 includes a container 20 and an ion-exchange tube sheet 22 accommodated in the container 20. The ion-exchange tube sheet 22 is formed by folding or winding one ion-exchange tube 24 more than once in a plane into a sheet form. The ion-exchange tube 24 is constituted by an ion-exchange membrane and has an inner diameter close to that of a tube 9 connected to a separation column. An inlet of the ion-exchange tube 24 is connected via a connector 26 to the tube 9 through which an eluate from a separation column flows. An outlet of the ion-exchange tube 24 is connected via a connector 28 to a tube 30 connected to an electrical conductivity measurement cell.

The container 20 includes a regenerant inlet 32 and a regenerant outlet 34 and provides a regenerant flow channel 36 so that a regenerant is allowed to flow on both sides of the plane of the ion-exchange tube sheet 22. The regenerant is used to regenerate ionic functional groups of the ion-exchange membrane.

Although not shown in FIG. 2, a pair of electrodes is provided in the regenerant flow channel 36 so as to be located on opposite sides of the plane of the ion-exchange tube sheet 22 to electrolyze a regenerant to generate hydrogen ions and hydroxide ions.

Figure 3A:
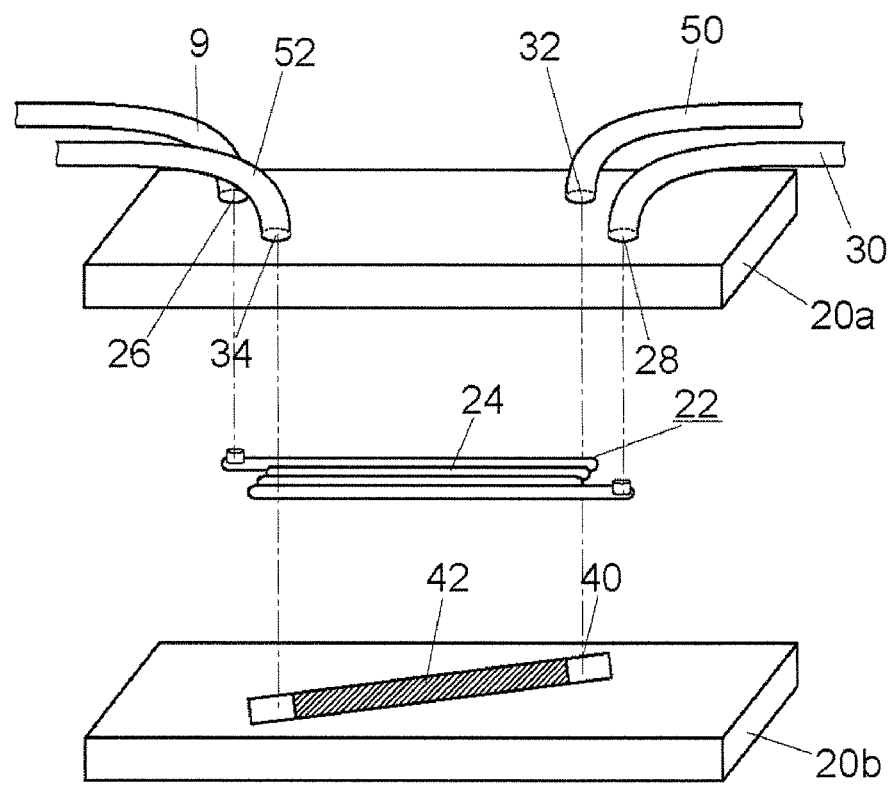
FIG. 3A is an exploded perspective view of a suppressor used in the ion chromatograph shown in FIG. 1.
Figure 3B:
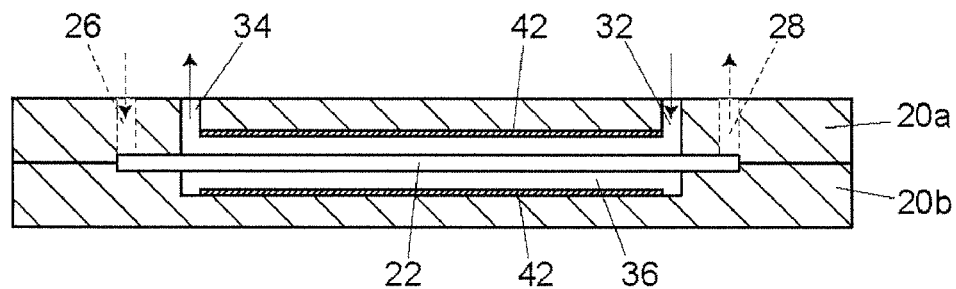
FIG. 3B is a sectional view of the suppressor shown in FIG. 3A.
Figure 4:
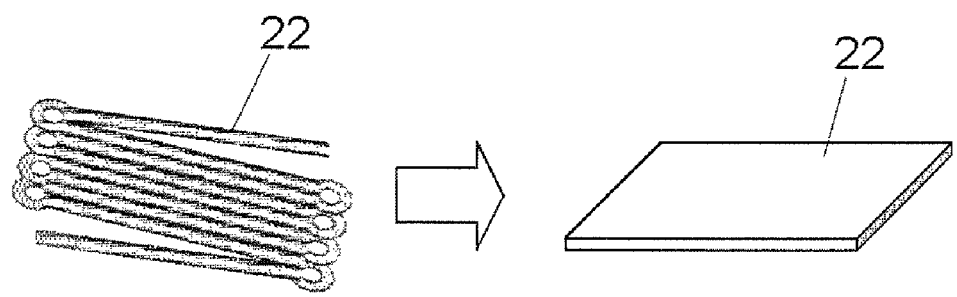
FIG. 4 shows one example of an ion-exchange tube sheet used in the suppressor shown in FIG. 3A, in which a plan view is on the left side and a schematic perspective view is on the right side.
Figure 5:
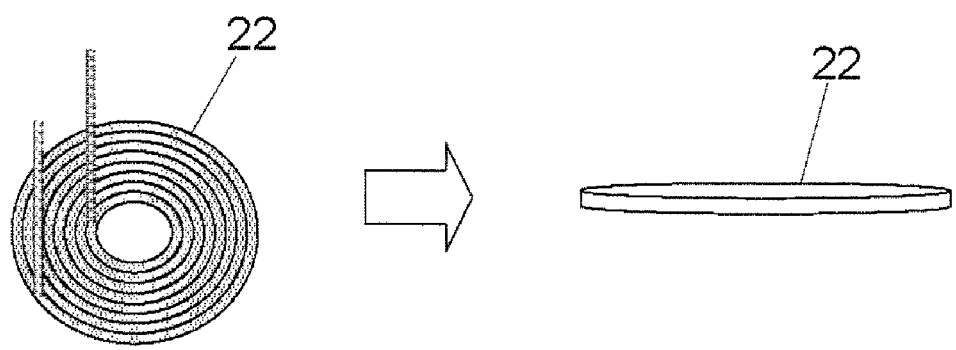
FIG. 5 shows another example of the ion-exchange tube sheet used in the suppressor shown in FIG. 3A, in which a plan view is on the left side and a schematic perspective view is on the right side.

This suppressor is more specifically described with reference to FIGS. 3A, 3B, 4, and 5. The container 20 is constituted by two substrates 20a and 20b between which the ion-exchange tube sheet 22 is to be interposed. In order to reduce the size of the suppressor, the ion-exchange tube sheet 22 is formed by folding the ion-exchange tube 24 in a zigzag manner as shown in FIG. 4 or by winding the ion-exchange tube 24 into a spiral as shown in FIG. 5.

A method for keeping the ion-exchange tube sheet 22 in a sheet form is not particularly limited. For example, a first method is one in which a recess is formed in each of the opposed surfaces of the substrates 20a and 20b and the ion-exchange tube 24 is accommodated in the recesses by folding or winding it, and a second method is one in which the ion-exchange tube 24 is folded or wound into a sheet form on an adhesive sheet to adhere adjacent tube surfaces to each other by an adhesive, and then the adhesive sheet is removed.

The substrate 20a has a groove 40 (not shown in FIG. 3A) provided in its surface opposed to the substrate 20b, and the substrate 20b also has a groove 40 provided in its surface opposed to the substrate 20a. The groove 40 provided in the substrate 20a and the groove 40 provided in the substrate 20b are opposed to each other with the ion-exchange tube sheet 22 being interposed between them to form together the regenerant flow channel 36.

In the groove 40 provided in the substrate 20a, an electrode 42 (not shown in FIG. 3A) is provided. Also in the groove 40 provided in the substrate 20b, an electrode 42 is provided. Each of the electrodes 42 has a lead wire (not shown) penetrating the substrate 20a or 20b and connected to an external power source. As shown in FIG. 3B, when the two substrates 20a and 20b are bonded together with the ion-exchange tube sheet 22 being interposed between them, the pair of electrodes 42 and 42 for electrolyzing a regenerant is arranged on opposite sides of the plane of the ion-exchange tube sheet 22 in the regenerant flow channel 36 without coming in contact with the ion-exchange tube sheet 22.

In order to allow an eluate from a separation column to flow through the ion-exchange tube 24 constituting the ion-exchange tube sheet 22, the connector 26 is provided so as to penetrate the substrate 20a. The tube 9 connected to a separation column is connected via the connector 26 to the inlet of the ion-exchange tube 24. The connector 28 is also provided so as to penetrate the substrate 20a. The outlet of the ion-exchange tube 24 is connected via the connector 28 to the tube 30 connected to an electrical conductivity measurement cell.

The tube 9 connected to a separation column, and the ion-exchange tube 24 have nearly the same inner diameter.

In order to allow a regenerant to flow through the regenerant flow channel 36, a connector 32 penetrating the substrate 20a is provided so as to be connected to one end of the regenerant flow channel 36. The connector 32 is connected to a tube 50 for supplying a regenerant. Further, a connector 34 penetrating the substrate 20a is provided so as to be connected to the other end of the regenerant flow channel 36. The connector 34 is connected to a tube 52 for discharging a regenerant having passed through the regenerant flow channel 36.

The substrates 20a and 20b are made of an inactive material to which ions are not adsorbed and from which ions are not eluted. Examples of such a material include an acrylic resin, a PEEK (polyether ether ketone) resin and the like. The tubes 9 and 30 are also made of an inactive material, such as a PEER resin, to which ions are not adsorbed and from which ions are not eluted. On the other hand, the material of the tubes 50 and 52 is not limited to such an inactive material, but is preferably one having chemical resistance such as a fluorine-based resin.

The ion-exchange tube 24 will be described with reference to some examples. A cation exchange tube can be obtained by, for example, forming a copolymer, obtained by copolymerizing the following compound A with the following compound B, into a tube and then saponifying the copolymer.

An anion exchange tube can be obtained, for example, in the following manner. A copolymer obtained by copolymerizing the following compound A with the following compound B is formed into a tube, saponified, treated with 2 N hydrochloric acid in accordance with a known method, converted to a sulfonyl chloride form, treated with hydrogen iodide, and subjected to alkaline washing to convert a membrane constituting the tube to a sodium carboxylate form. Then, the membrane is immersed in a 3.5 N aqueous hydrochloric acid solution, washed with water, and dried under a reduced pressure to obtain a tubular carboxyl-type copolymer. The carboxyl-type copolymer is converted to an acid halide form with, for example, thionyl chloride, and is then reacted with an amine such as N-(dimethylaminopropyl)ethylenediamine to form a polyamine. The polyamine is reduced with a reducing agent such as lithium aluminum hydride to obtain a target anion exchange tube.

(Compound A): $CF_2=CF_2$ (Compound B): $CF_2=CF-O-CF_2-CF(CF_3)-O-CF_2-CF_2-SO_2F$ In the case of the suppressor shown in FIGS. 3A and 3B, an eluate from a separation column for separating a sample is introduced into the suppressor through the tube 9. Segments separated by a separation column are subjected to ion exchange in the ion-exchange tube 24 of the suppressor. At this time, ions contained in the segments are exchanged through the ion-exchange tube 24 and the surface of the inner wall of the ion-exchange tune 24 is regenerated because a regenerant having a high ion concentration flows outside the ion-exchange tube 24. This makes it possible to continuously regenerate the ion-exchange tube 24. The segments having been subjected to ion exchange are sent to an electrical conductivity measurement cell of a detector through the tube 30 to detect target sample component ions.

A regenerant is introduced into the regenerant flow channel 36 through its inlet and then discharged through its outlet. The regenerant is pure water or an aqueous solution used to regenerate ionic functional groups of the ion-exchange membrane constituting the ion-exchange tube 24. The ionic functional groups are regenerated by hydrogen ions ($H^+$) or hydroxide ions ($OH^-$). More specifically, in a case where the ion-exchange membrane is a cation exchange membrane, the ionic functional groups are regenerated by hydrogen ions ($H^+$), and in a case where the ion-exchange membrane is an anion exchange membrane, the ionic functional groups are regenerated by hydroxide ions ($OH^-$).

According to this embodiment, as described above, the pair of electrodes 42 and 42 is provided in the regenerant flow channel 36. Therefore, $H^+$ and $OH^-$ can be resupplied by electrolyzing a regenerant through the application of a direct-current voltage or an alternating-current voltage to the electrodes 42 and 42.

In a case where the ion chromatograph according to this embodiment is intended to analyze anions, the ion-exchange membrane constituting the ion-exchange tube 24 is a cation exchange membrane. In this case, in the suppressor, nontarget cations contained in a column eluate flowing through the ion-exchange tube 24 are selectively removed because they are exchanged for hydrogen ions in the ion-exchange tube 24 by adsorption to the ion-exchange membrane and dialysis through the ion-exchange membrane. The hydrogen ions exchanged for nontarget cations react with hydroxide ions contained in the column eluate to form water. This reduces the electrical conductivity of the column eluate, thereby reducing noise detected in the electrical conductivity measurement cell of the detector. The nontarget cations removed by adsorption to the ion-exchange membrane constituting the ion-exchange tube 24 and dialysis through the ion-exchange membrane constituting the ion-exchange tube 24 are exchanged for hydrogen ions contained in a regenerant flowing through the regenerant flow channel 36 and are discharged into the regenerant.

In a case where the ion chromatograph according to this embodiment is intended to analyze cations, the ion-exchange membrane constituting the ion-exchange tube 24 is an anion exchange membrane. In this case, nontarget anions contained in a column eluate flowing through the ion-exchange tube 24 are selectively removed because they are exchanged for hydroxide ions in the ion-exchange tube 24. The hydroxide ions exchanged for nontarget anions react with hydrogen ions contained in the column eluate to form water. Therefore, also in this case, the electrical conductivity of the column eluate is reduced, thereby reducing noise detected in the electrical conductivity measurement cell. The nontarget anions removed by adsorption to the ion-exchange membrane constituting the ion-exchange tube 24 and dialysis through the ion-exchange membrane constituting the ion-exchange tube 24 are exchanged for hydroxide ions contained in a regenerant flowing through the regenerant flow channel 36 and are discharged into the regenerant.

What is claimed is:

1. A suppressor for suppressing a background electrical conductivity of an eluate from a separation column of an ion analyzer, comprising:
    an ion-exchange tube sheet through which an eluate from the separation column flows, the ion-exchange tube sheet being formed by folding or winding one ion-exchange tube more than once in a plane into a sheet form, the ion-exchange tube being constituted by an ion-exchange membrane and having an inner diameter close to that of a tube connected to the separation column; and
    a container in which the ion-exchange tube sheet is accommodated, the container providing a regenerant flow channel so that a regenerant for regenerating ionic functional groups of the ion-exchange membrane is allowed to flow on both sides of a plane of the ion-exchange tube sheet,
    wherein the ion-exchange tube sheet is formed only by the ion-exchange tube without a support,
    wherein the container is constituted by two substrates between which the ion-exchange tube sheet is to be interposed, and
    wherein both substrates each have one groove provided in each surface, the grooves provided in the two substrates being opposed to each other to form together the regenerant flow channel with the ion-exchange tube sheet being interposed between the grooves.

2. The suppressor according to claim 1,
    further comprising a pair of electrodes for electrolyzing the regenerant,
    wherein the electrodes are provided in the regenerant flow channel so as to be located on opposite sides of the ion-exchange tube sheet.

3. The suppressor according to claim 1,
    wherein the ion-exchange tube sheet is formed by densely arranging the ion-exchange tube in a plane so that adjacent tube surfaces are in contact with each other.

4. The suppressor according to claim 1,
    wherein the ion-exchange tube has an inner diameter of 500 μm or less.

5. The suppressor according to claim 4,
    wherein the ion-exchange tube has a wall thickness of 100 to 300 μm.

6. The suppressor according to claim 1,
    wherein the ion-exchange tube is made of a perfluorocarbon polymer having a functional group for ion exchange bonded thereto.

7. An ion chromatograph comprising:
    a separation column;
    an eluent supply channel for supplying an eluent to the separation column;
    an injector provided in the eluent supply channel for injecting a sample into the eluent supply channel;
    an electrical conductivity detector provided in an eluate flow channel through which an eluate from the separation column flows; and
    the suppressor according to claim 1 provided in the eluate flow channel between the separation column and the electrical conductivity detector.

* * * * *